United States Patent [19]

Ams et al.

[11] Patent Number: 5,131,381
[45] Date of Patent: Jul. 21, 1992

[54] APPARATUS FOR AUTOMATICALLY REGULATING THE SUPPLY OF LIGHT TO AN ENDOSCOPE

[75] Inventors: Felix Ams, Kämpfelbach; Roland Schäfer, Bretten-Dürrenbüchig, both of Fed. Rep. of Germany

[73] Assignee: Richard Wolf GmbH, Knittlingen, Fed. Rep. of Germany

[21] Appl. No.: 586,062

[22] Filed: Sep. 21, 1990

[30] Foreign Application Priority Data

Oct. 24, 1989 [DE] Fed. Rep. of Germany ....... 3935297

[51] Int. Cl.[5] .......................... A61B 1/04; H04N 7/18
[52] U.S. Cl. .......................................... 128/6; 358/98
[58] Field of Search ................. 128/4, 6; 358/98, 168, 358/202, 228

[56] References Cited

U.S. PATENT DOCUMENTS

| | | | |
|---|---|---|---|
| 4,025,955 | 5/1977 | Grallien et al. | 358/219 |
| 4,399,466 | 8/1983 | Stephenson | 358/228 |
| 4,638,366 | 1/1987 | Yoshimura et al. | 358/228 |
| 4,688,087 | 8/1987 | Ams et al. | |
| 4,791,480 | 12/1988 | Muranaka | 128/6 |
| 4,834,071 | 5/1989 | Hosoi et al. | 128/6 |
| 4,845,554 | 7/1989 | Kimura et al. | 358/98 |
| 4,866,526 | 9/1989 | Ams et al. | 358/98 |
| 4,868,645 | 9/1989 | Kobayashi | 128/6 |
| 4,873,572 | 10/1989 | Miwazaki et al. | 128/6 |
| 4,884,134 | 11/1989 | Tsuji et al. | 358/98 |
| 4,928,172 | 5/1990 | Uehara et al. | 358/98 |
| 4,951,135 | 8/1990 | Sasagawa et al. | 128/6 |
| 4,967,269 | 10/1990 | Sasagawa et al. | 128/6 |

FOREIGN PATENT DOCUMENTS

| | | |
|---|---|---|
| 3118341 | 5/1985 | Fed. Rep. of Germany . |
| 3509825 | 5/1988 | Fed. Rep. of Germany . |
| 3818125 | 5/1988 | Fed. Rep. of Germany . |
| 3743090 | 7/1988 | Fed. Rep. of Germany . |
| 2149264 | 6/1985 | United Kingdom . |

*Primary Examiner*—Stephen C. Pellegrino
*Assistant Examiner*—Ralph A. Lewis
*Attorney, Agent, or Firm*—Panitch Schwarze Jacobs & Nadel

[57] ABSTRACT

An apparatus for automatically regulating a light source for providing light for illuminating an object viewed by means of an endoscope equipped with a video camera, there is provided a signal processing device having a circuit for defining the density value of the video signal of each line of the camera image, by means of which circuit, the video signal emitted is passed to a comparator which compares it with a brightness threshold voltage which can be preset. A control signal for regulating the light source is determined by counting the image lines having a brightness exceeding the threshold voltage and linking the resultant count to a mathematical function. The actual value obtained from the video signal is independent of the area of the bright parts of the image and is, therefore, independent of the diameter of the image circle of the endoscope.

4 Claims, 1 Drawing Sheet

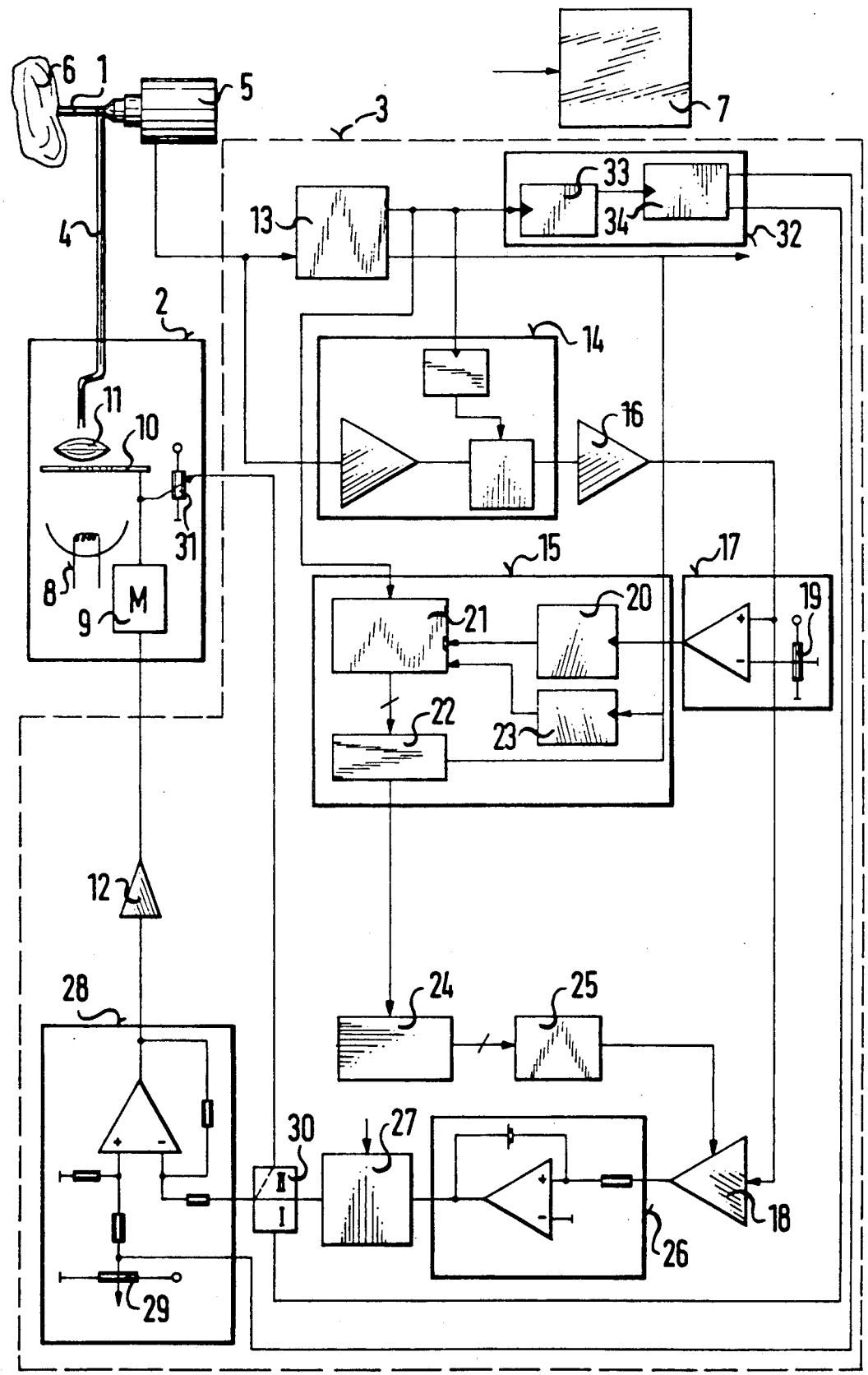

APPARATUS FOR AUTOMATICALLY REGULATING THE SUPPLY OF LIGHT TO AN ENDOSCOPE

FIELD OF THE INVENTION

The invention relates to apparatus for automatically regulating, by means of a video signal, a light source for providing light for illuminating an object viewed by means of an endoscope, the apparatus comprising a light conductor which transmits the illuminating light and is brought up to said object, an image transmitter connected to a video camera, a monitor for displaying the image recorded by the video camera and a signal processing device for the signal generated by the video camera.

BACKGROUND OF THE INVENTION

An endoscope is often used for viewing areas which are difficult to access, for example body cavities. In order to evaluate and document the state of an object viewed, a camera may be attached externally to the endoscope. If the camera is photographic said state can be photographically recorded. If a light converter element is used, for example a CCD element for converting optical signals into electrical video signals, records can be made by means of a video recorder. In order to produce images allowing precise diagnosis, the illumination of said object must be optimum. If a constant amount of light is delivered by the light source, said object may reflect the light to an undesirable extent, or may itself be under illuminated.

DE-B-31 18 341 discloses a light regulating system for an endoscope in which the image of the object is recorded by means of a television camera. The amount of light which impinges on the light conductor is regulated so that the voltage of the video signal is kept at an essentially constant voltage level regardless of any changes in the distance between the object viewed and the distal end of the endoscope.

Since the brightness of the image is regulated with the aid of the mean value of the video signal, the object viewed is not always correctly illuminated.

DE-A-37 43 090 discloses an illumination regulating system for an endoscope in which the illuminating light and the brightness of the object viewed are regulated automatically, regardless of the size of the image which can be transmitted by means of the image transmitter. The change in the level of the video signal as a result of using endoscopes having different image circle diameters and, therefore, different image ranges is compensated for in that width of the endoscopic image is scanned line by line, the greatest width being stored as the voltage level by a peak value holding circuit and being added onto the actual value of the video signal. The regulation of the video signal is in accordance with the greatest width, rather than the area of the image.

DE-A-35 09 825 discloses an illumination regulating system for a light projector, enabling an object to be illuminated correctly at its distance from the distal end of the endoscope and the amount of light to be limited to a maximum value. A theoretical-actual value comparison ensures that the video signal keeps within the maximum permitted amplitude. Although this regulating system prevents swamping out of the brightest parts of the image, the image background may become too dark.

SUMMARY OF THE INVENTION

An object of the invention is therefore to provide an automatic regulating system for the illuminating light of an endoscope which ensures optimum illumination of the object viewed, for video record purposes, both in the case of variable distances between the distal end of the endoscope and said object and regardless of the diameter of the image circle of the endoscope.

According to the present invention, therefore, for generating of actual value from the video signal, the signal processing device comprises a variable amplification amplifier, an integrating circuit and a sample-and-hold member, and, for generating the signal required for control of the amplifier, has a device for recording the number of lines of the image displayed on the monitor and a functional unit for performing a mathematical operation. The apparatus may be provided with a selector switch for automatic or manual light regulation, and a monitoring circuit for switching the apparatus to manual operation and closing an aperture through which light is transmitted to said object, in the absence of a video signal. Means may be provided with the aid of which the amount of light emitted by the light source can be determined from the position of the aperture and can be displayed.

Regulation of the illuminating light is in accordance with the area of the image, for better illumination.

BRIEF DESCRIPTION OF THE DRAWING

The single FIGURE is a block schematic diagram of apparatus according to an embodiment of the invention.

DETAILED DESCRIPTION OF THE INVENTION

The apparatus comprises an endoscope 1, a light source 2 for supplying the endoscope 1 with light for illuminating an object to be viewed thereby, and a signal processing device 3. In order to guide the illuminating light to the distal end of the endoscope 1, a light conductor 4 is connected to said distal end and to the light source 2. The endoscope 1 is equipped with a video camera 5 for recording the image transmitted from the endoscope 1, for example from a body cavity 6, converting it into a video signal and passing said signal to the signal processing device 3 and a display device 7. The video signal is displayed on the device 7 in the form of an image of the object viewed by the endoscope 1.

The light source 2 comprises a lamp 8, a motor 9, an aperture plate 10 and a lens device 11 for focusing and filtering the light emitted by the lamp 8, which is then passed to the light conductor 4. The motor 9 of the light source 2 serves to actuate the aperture plate 10, to open or close its aperture according to the amount of light required for illuminating said object. Control signals for this purpose are generated in the signal processing device 3 and are fed thereto by way of a motor drive unit 12 for controlling the speed of rotation and the direction of rotation of the motor 9.

In the signal processing device 3, the horizontal and vertical synchronising signals are filtered out of the video signal fed to the device 3, by a synchronising separating stage 13 and are fed to a counter circuit 15, a monitoring circuit 32 and a circuit 14 for defining the density value of the video signal of each line of the image of the camera 5. The video signal emitted by the circuit 14 is passed by way of an amplifier 16 to a comparator 17 and is applied at the same time to a variable amplification amplifier 18.

The comparator 17 compares the video signal with a brightness threshold voltage, which is adjustable by means of a control unit 19. If the image brightness in one line of the camera image exceeds the brightness represented by the brightness threshold voltage, a monoflop 20 is triggered in the counter circuit 15, to release the counter 21 of the counter circuit 15 for one line period so that the count can be increased by one by the horizontal synchronising signal. The image lines containing image information of a brightness exceeding the brightness threshold set are thereby counted. Lines having a brightness below the brightness threshold are ignored and are, therefore, not involved in the brightness regulation. The count is transferred to a circuit 22 for temporary data storage (latch) with the aid of the vertical synchronising signal at the end of the last image line and the counter 21 is set to zero by a time-lagged monoflop 23 triggered by the vertical synchronising signal.

The result of the count is then linked by multiplication in an EPROM 24 with a mathematical function stored therein, for example with quadratic function $1/x^2$. From the result of this operation, an analogue signal is produced by a digital/analogue converter 25 and is fed to the amplifier 18 to control the amplification thereof so that the greater is the area of the bright parts of the camera image, the smaller becomes the amplification of the amplifier 18.

The output signal of the amplifier 18 is integrated in an integrating circuit 26 over an image period and the result of such integration is stored by a sample-and-hold member 27, which is triggered by means of the vertical synchronising signal at the end of the last image line. The actual value derived from the video signal by the amplifier 18, the integrator 26 and the sample-and-hold member 27 is thus independent of the area of the bright parts of the image and thus of the image circle diameter of the endoscope 1. At the outlet of the sample-and-hold member 27, the result of the integration is available as the actual value for a theoretical-actual value comparison unit 28 which emits a control signal to the motor drive unit 12, which controls the motor 9 of the light source 2, according to the result of the comparison of the actual value and the theoretical value set by means of a control unit 29.

Instead of automatic regulation, that is to say the regulation of the intensity of the illumination by way of the video signal, said intensity may be adjusted by manual actuation of a control unit, whereby the amount of light emitted can be adjusted individually by the user. To this end, the signal processing device 3 contains a changeover switch 30 which can be changed over by the user from said automatic regulation (position I) to manual regulation (position II) of said amount of light. If manual regulation is selected, the actual value for the theoretical-actual value comparison is passed to the theoretical-actual value comparison unit 28 by way of an actual value emitter 31, which may be, for example, a potentiometer linked mechanically to the shaft of the aperture plate 10. The theoretical value in this case is still set by way of the control unit 29 and the output signal of the theoretical actual value comparison unit 28 controls the motor 9 of the light source 2 by way of the motor drive unit 12.

The automatic light source regulating system also comprises a monitoring circuit 32 which, in the absence of a video signal, ensures that the changeover switch 30 changes over from automatic to manual operation and the aperture of the plate 10 of the light source 2 is closed, thereby preventing the user from being dazzled, for example, if the camera is disconnected, or the patient being subjected to high thermal stresses if the regulating system were completely to open the aperture of the plate 10 by reason of the absence of a video signal. The monitoring circuit 32 also contains a monoflop 33 which is triggered by the horizontal synchronising signal and can subsequently be triggered, and a monoflop 34, for example, a negatively edge-triggered monoflop, downstream of the monoflop 33. The monitoring circuit 32 delivers no output signals if a video signal is present. Only when the horizontal synchronising signal is absent is the monoflop 34 triggered by the negative edge of the output signal of the monoflop 33, and the monitoring circuit 32 delivers a short and a longer pulse as output signals. The short pulse is passed to the changeover switch 30, to change it over to manual operation. At the same time the longer pulse adjusts the theoretical value in the theoretical-actual value comparison unit 28 so that the motor drive unit 12 ensures that the aperture of the plate 10 is closed by means of the output signal of the theoretical-actual value comparison unit.

The extent of the aperture may be displayed visually by means of a further device, as an indication of the amount of light emitted.

What is claimed is:

1. Apparatus for automatically regulation, by means of a video signal, a light source for providing light for the illumination of an object viewed by means of an endoscope, the light source having an aperture plate, the apparatus comprising:
   a light conductor for transmitting said illuminating light from the light source to the distal end of the endoscope including means for connecting the light conductor to the light source;
   a video camera for recording an image transmitted from the endoscope;
   an image transmitter connected to the video camera for transmitting said image thereto;
   a monitor connected to the video camera for displaying the video image recorded thereby; and
   a signal processing device for processing a video image signal generated by the video camera, the processed signal controlling the aperture plate; wherein for generating an actual value from said video signal, the signal processing device comprises a variable amplification amplifier, an integrating circuit connected to said amplifier, said integrating circuit receiving an output signal of said amplifier, and a sample-and-hold member connected to said integrating circuit, said sample-and-hold member storing a result from said integrating circuit; and for generating a signal for the control of said amplifier, a device connected to the video camera for recording the number of lines of the video image having a brightness exceeding a predetermined brightness threshold displayed by said monitor and recorded by the video camera; and a functional unit for performing a mathematical operation connected to the line recording device, said actual value being independent of the diameter of an image circle of the endoscope.

2. Apparatus as claimed in claim 1, further comprising means for manual regulation of the light source and a selector switch operable to switch said apparatus between automatic and manual regulation of said light source.

3. Apparatus as claimed in claim 1, comprising a monitoring circuit for changing said apparatus over from automatic to manual regulation of said light source, and for closing an aperture for admitting light from said light source to said light conductor; in the absence of said video signal.

4. Apparatus as claimed in claim 1, wherein said recording device is arranged to count only those of said lines the brightness of which exceeds an adjustable limit value.

* * * * *